United States Patent [19]
Gupta

[11] 4,203,317
[45] May 20, 1980

[54] POROSIMETER

[76] Inventor: Krishna M. Gupta, F-24, Lansing West, Ithaca, N.Y. 14850

[21] Appl. No.: 917,347

[22] Filed: Jun. 20, 1978

[51] Int. Cl.² .......................................... G01N 15/08
[52] U.S. Cl. ..................................................... 73/38
[58] Field of Search ........................... 73/38, 314, 307

[56] References Cited

U.S. PATENT DOCUMENTS

| | | | |
|---|---|---|---|
| 2,886,964 | 5/1959 | Shapiro et al. | 73/38 |
| 3,022,657 | 2/1962 | Hampton . | |
| 3,073,357 | 1/1963 | Hampton . | |
| 3,199,341 | 8/1965 | Hever et al. | 73/38 |
| 3,371,520 | 3/1968 | Slone et al. | 73/38 |
| 3,438,245 | 4/1969 | Winslow . | |
| 3,501,944 | 3/1970 | Winslow . | |
| 3,859,843 | 1/1975 | Lowell | 73/38 |

Primary Examiner—Anthony V. Ciarlante
Attorney, Agent, or Firm—Spellman, Joel and Pelton

[57] ABSTRACT

A porosimeter comprises a tube of non-magnetic material connected at one end to a sample chamber capable, like the tube, of withstanding high internal pressures, means to exhaust the sample chamber and tube, means to fill the chamber and tube with mercury, means to deliver to the tube under adjustable pressure a fluid of density different from that of mercury, a float of magnetic material and of intermediate density disposed in the tube, and a differential transformer in which the float acts as a core to indicate the position of the float.

20 Claims, 4 Drawing Figures

POROSIMETER

BACKGROUND OF THE INVENTION

1. Field of the Invention

The present invention pertains to and lies within the field of porosimetry, i.e. the measurement of the porosity of substances, and more particularly to porosimetry by the mecury intrusion method. In this method, the porosity of a substance is measured by measurement of the volumes of a liquid, usually mercury, which at various hydrostatic pressures are forced into the pores of a sample of the substance.

2. Description of the Prior Art

Porosimeters are known in which fluid pressure is applied to a mercury column in a tube connecting with an otherwise closed sample chamber. In the prior art porosimeters of this type of which I am aware, the volume of mercury entering the pores of the sample is measured by measuring the motion, toward the sample chamber with increasing applied pressure, of the end of the mercury column remote from the sample chamber. The measurement has been made visually, as in U.S. Pat. Nos. 2,886,964, 3,022,657 and 3,073,357 by making the tube transparent and by noting the position of the end of the mercury column against graduations on the tube. Alternatively a movable probe, passing through a pressure-tight seal at the end of the tube far from the sample chamber, may be employed to give indications of the position of the end of the mercury column, upon the making and breaking of electrical contact between the probe and the mercury, as in U.S. Pat. No. 3,371,520. It has also been proposed to employ the mercury column in an electrical circuit of resistance or capacitance varying with the length of the mercury column, so as to obtain from the circuit indications of that length. See U.S. Pat. No. 3,438,245.

SUMMARY OF THE INVENTION

According to the present invention instead, there is employed to give indications of the length of the mercury column a float, of density intermediate between that of the mercury (or other pore-penetrating fluid employed) and that of a lighter fluid, e.g. alcohol, used to apply pressure to the mercury. The float moves with the interface between the mercury and the pressure-applying fluid as the pressure of the latter is varied, and the float is incorporated as a coupling element of a transducer or transmission line, the degree of coupling between the ends of the transducer varying with the position of the float vis-a-vis the other elements of the transducer. In a preferred embodiment the float is a ferro-magnetic member and the transducer takes the form of an electrical transformer in which the float constitutes a movable core, the transformer having a primary winding and two oppositely wound and series-connected secondary windings, all three windings being coaxially disposed about the tube containing the float. The transformer is thus a differential transformer, and the magnitude and phase of its output voltage are a function of the displacement of the float from a position of zero or minimum output. The output voltage can be displayed on a display calibrated in units of volume of displacement of the mercury column. In another presently preferred embodiment of the invention the transformer windings are supported together for motion lengthwise of the tube under control of a mechanism responsive to the output voltage, so that transformer position is an indication of volume displacement of the column.

BRIEF DESCRIPTION OF THE DRAWINGS

The invention will now be further described in terms of two presently preferred exemplary embodiments thereof and by reference to the accompanying drawing in which.

DESCRIPTION OF THE PREFERRED EMBODIMENTS

Figure 1:
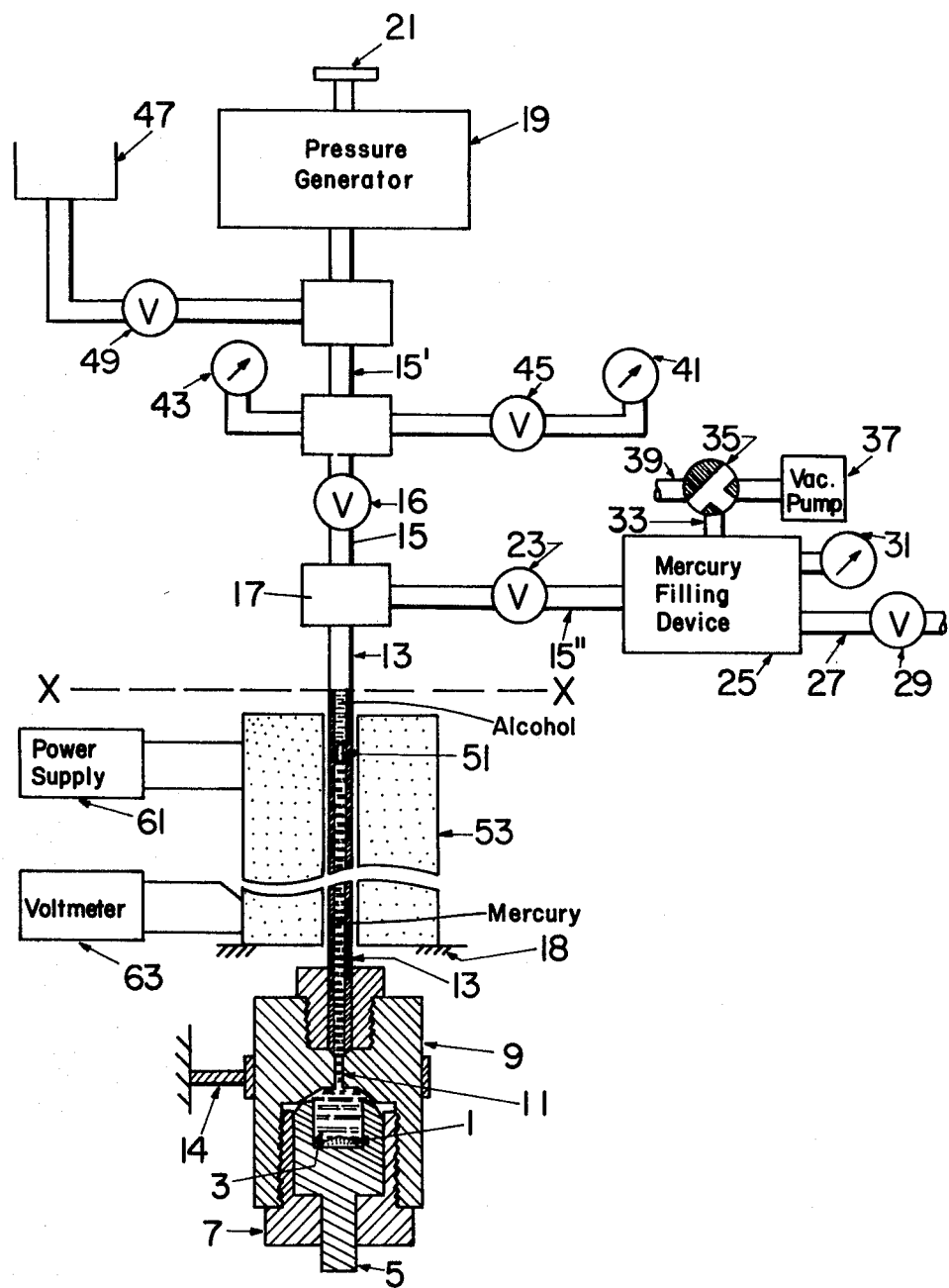
FIG. 1 is a representation, partly diagrammatic, of a first presently preferred embodiment of the invention, showing however in axial section the sample chamber, the small bore tube by which displacements of mercury into the specimen are measured, and the differential transformer cooperating with a float in that tube.

Referring to FIG. 1, a sample 1 of a material whose porosity is to be measured is contained in a sample holding cavity 3 defined by a plug 5 drawn by a removable threaded collar 7 into pressure-tight sealing relation against an annular block 9 having a central bore 11 which thus communicates with the cavity 3. The elements 5, 7 and 9 may be of steel. O-rings, gaskets and the like may be employed conventionally to seal these elements in pressure-tight relation to each other and to the tube 13 to be described next.

A tube 13 of uniform bore, which may for example be of the order of 0.050 inches in inside diameter, is threadedly engaged in pressure-tight fashion with the block 9 at the bore 11 therein, so that the interior of the tube communicates likewise with the sample cavity. The tube 13 is made of non-magnetic material, and need not be transparent. A suitable material is a non-magnetic stainless steel such as that known as AISI (American Iron and Steel Institute) 340 or 316. The elements 5, 7, 9 and 13, shown in axial section in FIG. 1, are supported in a stationary position, as indicated by the supports 14. Preferably the tube 13 is substantially upright with the chamber 3 below that tube.

At its upper end the tube 13 communicates, in gas- and liquid-tight fashion, with a hydraulic conduit 15, for example via a coupling indicated at 17, which may be detachable. Conduit 15 connects via a valve 16 to a pressure generator 19 by means of which controllable hydraulic pressures may be built up in the conduit and hence in the cavity 3, at values ranging from one atmosphere absolute up to, for example, several hundreds or thousands of pounds per square inch. Devices of this type are conventional and well known. An operating member for the building up of pressure is indicated by means of a hand wheel 21.

The conduit 13 and coupling 17 connect through a valve 23 to a mercury filling device 25 to be further described in connection with FIG. 2. The device 25 has a discharge line 27 leading to atmosphere through a valve 29, and it has a pressure gauge or indicator 31. A conduit 33 leads from the device 25 through a three-way valve 35 to a vacuum pump 37 or to a conduit 39 open to the atmosphere.

Low and high range pressure gauges 41 and 43 permit reading the pressure delivered by the generator 19, a valve 45 being provided to isolate gauge 41 from that output when the delivered pressures are above its range. A vessel 47, which may be an open vessel, connects through a valve 49 to the conduit, indicated at 15', which leads from the generator 19 through valve 16 to conduit 15.

Inside the tube 13 there is disposed a float 51 of ferromagnetic material, dimensioned to move freely within the tube. The float may thus have the shape of a right circular cylinder. It may be made of any one of a number of high permeability ferromagnetic alloys. One such is Kovar.

Surrounding the tube 13 and held in stationary position with respect thereto as indicated by the supports 18 is a differential transformer 53. The transformer has a primary winding 55 (FIG. 4) and two secondary windings 57 and 59 connected in series-opposing relation as indicated by the dots in FIG. 4. The primary winding is fed from a power supply 61, and the free terminals of the secondaries connect to a voltmeter 63, which may be calibrated in terms of displacement of the float 51 from a zero position, and thereby in terms of units of volume of mercury displaced in the tube.

Figure 4:
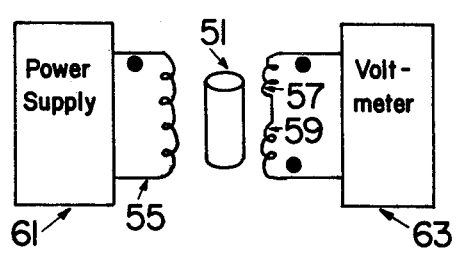
FIG. 4 is a schematic circuit diagram of a form of differential transformer which can be used in the apparatus of the invention.

The showing of FIG. 4 is purely schematic; the three windings may be coaxial of each other and of the tube 13, surrounding the latter.

Figure 2:
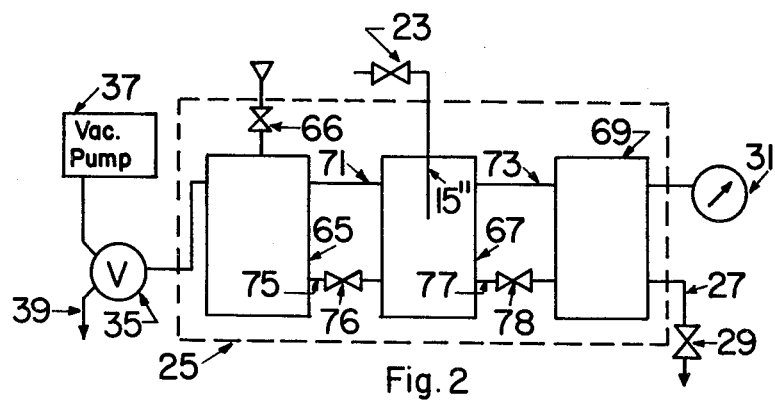
FIG. 2 is a schematic diagram of the mercury filling device of the embodiment of FIG. 1.

The filling device 25 of FIG. 1 is further illustrated in schematic fashion, in FIG. 2. It comprises three closed vessels 65, 67 and 69. Hydraulic lines 71 and 73 (i.e. conduits) interconnect the upper portions of these vessels, and similar lines 75 and 77, with valves 76 and 78 therein respectively, interconnect the lower portions thereof. The extension 15" of conduit 15 between valve 23 and the device 25 penetrates into vessel 67 part way to the bottom thereof. Mercury may be introduced into the vessel 65 from any suitable source of supply through a valve 66.

The apparatus of FIG. 1 may be operated in the following fashion: A supply of mercury is introduced into the vessel 65, and of alcohol into the vessel 49. A weighed sample of material whose porosity is to be investigated is inserted into the chamber 3 and the plug 5 is assembled to the block 9 and tube 13 by means of the collar 7. With valves 16, 29, 49, 76 and 78 closed, valves 23 and 45 open, and valve 35 set to connect the vacuum pump 37 to line 33, the pump is energized to exhaust the system below valve 16 down to a suitable low pressure. Valve 76 is next opened to permit mercury to flow from vessel 65 into 67 to immerse the lower, open end of conduit 15" in the mercury sufficiently to permit filling of the tube 13 with mercury. Valve 35 is then carefully manipulated to allow air to enter slowly into the vessels 65, 67 and 69, driving the mercury up into conduit 15" and through the valve 23 into the tube 13 and sample chamber 3. With the power supply 61 energized, a pre-chosen signal value will be obtained on the voltmeter 63 when the mercury has risen in the tube 13 sufficiently to lift the float 51 into the range of positions over which the float significantly affects the coupling of the primary winding to the secondary windings of transformer 53, and in particular into the position at which the algebraic sum of the couplings between the primary and the two secondaries yields the chosen signal level. The transformer may be so constructed that its output signal varies, algebraically, in close proportionality with the position of the float over a wide range of positions.

Mercury is next withdrawn from vessel 67 into vessel 69 sufficiently to expose the lower end of conduit 15", and valve 23 is fully opened. Then the pressure in tube 13 above the mercury may be gradually raised to atmospheric by manipulation of valve 35. The pressure being noted on gauge 31 and the height of the mercury column being read from voltmeter 63, suitably calibrated, data are obtained on the volumes of mercury forced into the pores of the sample at these various pressures. For accurate results, account must be taken not only of the absolute gas pressure above the mercury, readable on gauge 31, but of the height of the mercury column (i.e. its hydrostatic head) and of the effective accretion to that head contributed by the weight of the float 51.

For the application of higher pressures, the space above the mercury column is filled with a fluid, preferably substantially incompressible, so that the pressure generator 19 may effectively apply pressure to the mercury. To this end valve 23 is closed and valves 16 and 49 are opened. This permits alcohol to flow from the open vessel 47 into and substantially to fill the conduits 15 and 15'. Special steps may be taken to purge the system of the air admitted at valve 35 in bringing the pressure above the mercury to atmospheric; such steps may or may not be necessary according to circumstances.

In FIG. 1, heavy interrupted horizontal hatching lines are used to indicate mercury inside tube 13, extending from cavity 3 up to the float, which is partly immersed in the mercury. Lighter interrupted horizontal hatching lines above the mercury indicate alcohol or whatever other fluid, introduced from vessel 47, fills the upper end of tube 13 and conduits 15 and 15' as well. The float 51 is made of material having a density smaller than that of mercury but greater than that of this other fluid. By noting the volume of mercury forced into or expelled from a sample of known weight with increase or decrease in applied pressure, it is possible to calculate the distribution of pores among various diameters, their aggregate volume, the surface area of the material of the sample per unit weight, and also the density of the material.

Figure 3:
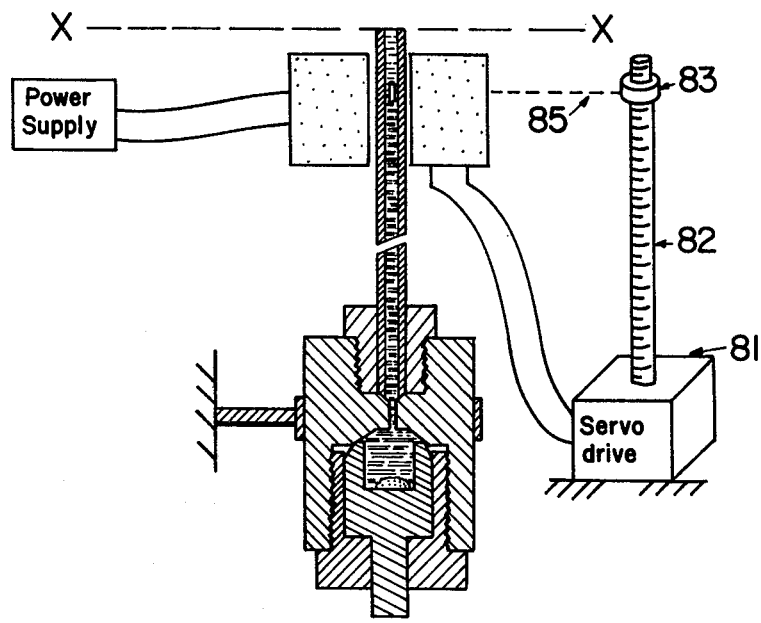
FIG. 3 is a representation of apparatus which, replacing the apparatus below the dash line X—X in FIG. 1 and combined with the apparatus above that line, constitutes a second presently preferred embodiment of the invention.

FIG. 3 illustrates a modification of the apparatus of FIGS. 1, 2 and 4, the apparatus of FIG. 3 being combined with the apparatus above dash line X—X of FIG. 1 to produce this alternative embodiment of the apparatus of the invention. In this alternative embodiment the transformer 53 is supported on guides for motion lengthwise of the tube 13. The tube 13 itself may constitute such guide means, or a part thereof. The output leads from the transformer connect to a stationary servo device 81, whose mechanized output member is a lead screw 82. A nut 83, restrained from rotation, is engaged on the lead screw and is coupled by a mechanical link 85 to transformer 53. An index on or coupled to the transformer and movable past a stationary scale, e.g. oriented parallel to the path of transformer motion, or alternatively for example a counter on the revolutions of the lead screw, may permit direct reading of mercury volumes displaced.

In FIG. 2, the vessel 69 is a temporary storage vessel into which mercury from vessel 67 may be drawn off to as to disengage the lower end of conduit 15" from the mercury, when as above described the pressure in tube 13 above the mercury is to be raised to atmospheric by manipulation of valve 35.

While the invention has been described hereinabove in terms of two presently preferred embodiments thereof, the invention itself is not limited thereto, but rather comprehends all modifications of and departures from those embodiments properly falling within the spirit and scope of the appended claims. To mention only one such modification, other forms of transducer may be employed in place of the differential transformer 53 with its movable ferromagnetic core formed by the float 51.

I claim:

1. A porosimeter comprising, in combination:
   (a) an opaque, sample chamber constructed of metal for holding a sample of material whose porosity is to be measured;
   (b) an opaque, non-horizontal tube constructed of metal having an upper end and a lower end, the lower end of said tube being connected to said chamber;
   (c) means connected to said tube for filling said chamber and said tube with a liquid which is non-wettable with respect to said sample;
   (d) means connected to said upper end of said tube for applying a fluid at various pressures to the upper end of said tube, said fluid having a lower density than said liquid;
   (e) means for measuring the height of the upper of said liquid in said tube during application of said various pressures;
   whereby the porosity of said sample in said chamber may be determined from the height measurements and the respective, various pressures.

2. The porosimeter defined in claim 1, wherein said measuring means comprises a float arranged in said tube and means for determining the position of said float in said tube, said float having a density which is greater than said fluid and less than said liquid.

3. A porosimeter according to claim 2, wherein said float is of magnetic material and wherein said position-determining means include a transformer having primary and secondary windings whose magnetic coupling varies with the position of said float lengthwise of said tube.

4. A porosimeter according to claim 3 wherein said transformer is a differential transformer.

5. A porosimeter according to claim 4 wherein said position-determining means include means to display the output voltage of said transformer.

6. A porosimeter according to claim 4 wherein said transformer is mounted for motion lengthwise of said tube, said porosimeter further comprising a servo-mechanism receiving as error signal the output of said transformer, said servo-mechanism being mechanically coupled to said transformer.

7. A porosimeter according to claim 2, wherein said position-determining means comprise means defining with said float a transducer.

8. A porosimeter according to claim 2, wherein said means to fill said chamber include a supply vessel connecting with a delivery vessel, conduit means extending downwardly into said delivery vessel, a controllable conduit for liquid flow between said vessels, and means to control the gas pressure in said vessels.

9. A porosimeter according to claim 2, wherein said position-determining means include a transducer in which said float constitutes a variable coupling element.

10. The porosimeter according to claim 1 wherein said filling means include:
    (a) a supply vessel;
    (b) a delivery vessel;
    (c) first controllable conduit means extending into said delivery vessel and connected to said tube;
    (d) second controllable conduit means connecting said supply vessel, at its lower portion, with said delivery vessel; and
    (e) means for applying a gas under pressure to at least one of said vessels.

11. A porosimeter according to claim 10, wherein said first controllable conduit means extends downwardly into said delivery vessel to a point above the bottom of said vessel.

12. A porosimeter according to claim 10, wherein said gas applying means is operative to apply said gas to said supply vessel.

13. A porosimeter according to claim 10, further comprising third conduit means connecting said supply vessel, at its upper portion, to said delivery vessel.

14. A porosimeter according to claim 10, further comprising means for applying said liquid to said supply vessel.

15. A porosimeter according to claim 10, further comprising a removal vessel and third controllable conduit means connecting said delivery vessel, at its lower portion, to said removal vessel.

16. A porosimeter according to claim 15, further comprising a fourth conduit means connecting said delivery vessel, at its upper portion, to said removal vessel.

17. A porosimeter according to claim 15, further comprising means for draining said liquid from said removal vessel.

18. The porosimeter defined in claim 1, wherein said chamber is made of stainless steel.

19. The porosimeter defined in claim 1, wherein said tube is made of stainless steel.

20. The porosimeter defined in claim 1, wherein said tube is made of non-magnetic material.

* * * * *